(12) United States Patent
Akiyama et al.

(10) Patent No.: US 9,698,705 B2
(45) Date of Patent: Jul. 4, 2017

(54) ELECTROMECHANICAL TRANSDUCER DEVICE AND ANALYTE INFORMATION ACQUIRING APPARATUS

(71) Applicant: CANON KABUSHIKI KAISHA, Tokyo (JP)

(72) Inventors: Takahiro Akiyama, Kawasaki (JP); Chienliu Chang, Menlo Park, CA (US)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/841,853

(22) Filed: Sep. 1, 2015

(65) Prior Publication Data
US 2015/0372618 A1 Dec. 24, 2015

Related U.S. Application Data

(63) Continuation of application No. 13/702,059, filed as application No. PCT/JP2011/003111 on Jun. 2, 2011, now Pat. No. 9,154,057.

(30) Foreign Application Priority Data

Jun. 7, 2010 (JP) .................. 2010-130295

(51) Int. Cl.
  *B06B 1/06* (2006.01)
  *H02N 1/08* (2006.01)
  (Continued)

(52) U.S. Cl.
  CPC .............. *H02N 1/08* (2013.01); *B06B 1/067* (2013.01); *G01N 29/00* (2013.01);
  (Continued)

(58) Field of Classification Search
  CPC .......... H02N 11/002; H02N 1/00; H02N 1/08; G01N 29/00; G01N 29/2418; G01N 2291/101; B06B 1/067
  (Continued)

(56) References Cited

U.S. PATENT DOCUMENTS 6,831,394 B2  12/2004  Baumgartner
7,321,181 B2  1/2008   Khuri-Yakub
(Continued)

FOREIGN PATENT DOCUMENTS

CN   101573861 A   11/2009
CN   101615863 A   12/2009
WO   2009/088307 A1  7/2009

*Primary Examiner* — Laura Martin
*Assistant Examiner* — Rose M Miller
(74) *Attorney, Agent, or Firm* — Canon USA, Inc. IP Division

(57) ABSTRACT

To suggest an electromechanical transducer device with a high S/N ratio, an electromechanical transducer device includes a first substrate; electromechanical transducer elements two-dimensionally arrayed on a front surface of the first substrate and configured to provide conversion between acoustic waves and electric signals; an electric wiring substrate that is a second substrate electrically connected with a back surface of the first substrate; a first acoustic matching layer provided between the first substrate and the second substrate; an acoustic attenuating member arranged on a back surface of the second substrate; and a second acoustic matching layer provided between the second substrate and the acoustic attenuating member.

12 Claims, 5 Drawing Sheets

(51) Int. Cl.
*G01N 29/00* (2006.01)
*H02N 1/00* (2006.01)
*H02N 11/00* (2006.01)
*G01N 29/24* (2006.01)

(52) U.S. Cl.
CPC ........... *G01N 29/2418* (2013.01); *H02N 1/00* (2013.01); *H02N 11/002* (2013.01); *G01N 2291/101* (2013.01)

(58) Field of Classification Search
USPC .......................... 73/632, 643; 310/326–327
See application file for complete search history.

(56) References Cited

U.S. PATENT DOCUMENTS

| | | |
|---|---|---|
| 2002/0048219 A1 | 4/2002 | Ladabaum |
| 2003/0028108 A1 | 2/2003 | Miller |
| 2005/0043628 A1* | 2/2005 | Baumgartner ........ B06B 1/0292 600/459 |
| 2007/0035204 A1* | 2/2007 | Angelsen ................ B06B 1/064 310/311 |
| 2008/0154135 A1* | 6/2008 | Kimura .................... A61B 8/12 600/463 |
| 2011/0018387 A1* | 1/2011 | Ogawa ................. B06B 1/0292 310/300 |
| 2011/0181149 A1* | 7/2011 | Shikata ................ B06B 1/0629 310/327 |

\* cited by examiner

--PRIOR ART--

ELECTROMECHANICAL TRANSDUCER DEVICE AND ANALYTE INFORMATION ACQUIRING APPARATUS

CROSS-REFERENCE TO RELATED APPLICATIONS

This application is a Continuation of co-pending U.S. patent application Ser. No. 13/702,059 filed Dec. 4, 2012, which is a National Phase application of International Application PCT/JP2011/003111, filed Jun. 2, 2011, which claims the benefit of Japanese Patent Application No. 2010-130295, filed Jun. 7, 2010. The disclosures of the above-named applications are hereby incorporated by reference herein in their entirety.

TECHNICAL FIELD

The present invention relates to an electromechanical transducer device (representatively, capacitive electromechanical transducer device) and an analyte information acquiring apparatus.

BACKGROUND ART

An electromechanical transducer device that is used as an ultrasonic transducer device (also referred to as ultrasonic transducer) is used in, for example, a diagnostic apparatus for a tumor etc. in a human body by transmitting and receiving ultrasonic waves, which are acoustic waves.

In recent years, a capacitive electromechanical transducer device (capacitive micromachined ultrasonic transducer, CMUT) using a micromachining technique is being actively studied. This CMUT transmits and receives ultrasonic waves by using a vibrating membrane. Also, this CMUT has a wide frequency band of ultrasonic waves that can be transmitted and received (i.e., CMUT has wide-band characteristics). Ultrasonic diagnosis using this CMUT and hence having higher precision than that of a medical diagnostic modality in the past is receiving attention as a promising technique.

In general, imaging apparatuses using X-rays, ultrasonic waves, and magnetic resonance imaging (MRI) are frequently used in medical fields. Also, studies on an optical imaging apparatus that obtains in vivo information by causing light emitted from a light source such as a laser to propagate into an analyte such as a living body and detecting the propagation light are being actively promoted in medical fields. There is suggested photoacoustic tomography (PAT) as one of such optical imaging techniques.

PAT is a technique that irradiates an analyte with pulsed light generated from a light source, detects acoustic waves (representatively, ultrasonic waves) generated from living tissues absorbing energy of light propagating through and diffused in the analyte at a plurality of detection positions, analyzes signals of these acoustic waves, and visualizes information relating to optical characteristic values of the inside of the analyte. Accordingly, information relating to optical-characteristic-value distribution of the inside of the analyte, or more particularly to optical-energy-absorption-density distribution can be obtained.

In an electromechanical transducer device (also referred to as ultrasonic transducer device) including electromechanical transducer elements that are formed on a substrate, part of incident ultrasonic waves may interfere with reflection waves that are reflected by a back surface of the substrate (a surface opposite to a surface of the substrate with the electromechanical transducer elements formed) and generate noise.

This noise problem has been recognized by certain degree in the past. Even with a technique of related art, as long as electromechanical transducer elements with a high-frequency region of several megahertz or higher (for example, 2 to 3 MHz or higher) are used, frequencies, which may cause noise, are high and are likely attenuated. Hence, the noise problem may be addressed by certain degree by providing an acoustic attenuating member on the back surface of the substrate. With a frequency that resonates within a substrate like PTL 1, noise can be reduced by certain degree by matching an acoustic impedance of the acoustic attenuating member to an acoustic impedance of the substrate. However, in the case of CMUT, since the frequency band is wide, the frequency band may contain ultrasonic waves with a frequency lower than 2 MHz. The ultrasonic waves with the frequency lower than 2 MHz are hardly attenuated, and easily pass through the substrate. Hence, the measure of related art only has a limited effect.

FIG. 5 shows a configuration of related art. In the configuration of related art (PTL 1), an acoustic attenuating member 14 is provided on a back surface of a substrate 12, and an electric signal is acquired from end portions of the substrate 12 through electric wiring 13.

The above-described ultrasonic transducer device used for the above-described ultrasonic diagnosis includes transducer elements that are two-dimensionally arrayed (arrayed in a plane) on a front surface of the substrate. For an array with a higher density, the transducer device has a structure in which the front surface and the back surface of the substrate are electrically connected and electric wiring is drawn from the back surface of the substrate. To acquire signals of the two-dimensionally arrayed electromechanical transducer elements, an electric wiring substrate has to be provided on the back surface of the substrate and the electric wiring substrate has to be electrically connected with the substrate. With this configuration, since the distance between the substrate and the electric wiring substrate is small, the acoustic attenuation on the back surface of the substrate results in that the reflection waves from the back surface of the substrate and the electric wiring substrate affects the electromechanical transducer elements, and hence a signal-to-noise (S/N) ratio is degraded. Particularly in a frequency band with 1 MHz or lower, wavelengths are large and attenuation is small. The influence becomes noticeable. Also, to reduce noise crosstalk, there is a method in which an electric wiring substrate or an integrated circuit is arranged on the back surface of the substrate, and the electric wiring substrate or the integrated circuit is electrically connected with the back surface of the substrate. At this time, the distance between the back surface of the substrate and the electric wiring substrate or the integrated circuit is as small as several hundred micrometers. Hence, even if the acoustic attenuating member of related art is provided on the back surface of the substrate, low-frequency acoustic waves easily reach the electric wiring substrate, and reflection waves may become noise.

PTL 2 describes that projections and depressions are formed on a back surface of an electric wiring substrate to reduce reflection waves. However, to attenuate acoustic waves with wavelengths larger than a predetermined value (acoustic waves with frequencies lower than 2 MHz), large projections and depressions are required. At the same time, the thickness of the electric wiring substrate is limited in a fabrication process and a soldering and mounting process.

CITATION LIST

Patent Literature

[PTL 1] U.S. Pat. No. 6,831,394
[PTL 2] U.S. Pat. No. 7,321,181

SUMMARY OF INVENTION

The present invention provides a configuration of an electromechanical transducer device with a wider band and a higher S/N ratio than those of related art by reducing reflection-wave noise in a low-frequency band.

An electromechanical transducer device according to an aspect of the invention includes a first substrate; electromechanical transducer elements two-dimensionally arrayed on a front surface of the first substrate and configured to provide conversion between acoustic waves and electric signals; an electric wiring substrate that is a second substrate electrically connected with a back surface of the first substrate; a first acoustic matching layer provided between the first substrate and the second substrate; an acoustic attenuating member arranged on a back surface of the second substrate; and a second acoustic matching layer provided between the second substrate and the acoustic attenuating member.

An analyte information acquiring apparatus according to another aspect of the invention includes the electromechanical transducer device according to the above aspect; a light source configured to emit pulsed light; and a signal processing system configured to process a signal that is detected by the electromechanical transducer device. The analyte information acquiring apparatus irradiates an analyte with the light emitted from the light source, detects an acoustic wave generated as the result of a photoacoustic effect of the light emitted on the analyte by the electromechanical transducer device, and acquires physical information of inside of the analyte through processing by the signal processing system.

With any of the aspects of the present invention, the acoustic matching layer and the acoustic attenuating member are provided on the back surface of the substrate. Accordingly, when ultrasonic waves with frequencies of several megahertz or lower are used, noise, which is generated by reflection from the back surface of the substrate and which is applied to the electromechanical transducer elements arranged on the front surface of the substrate, can be reduced.

DESCRIPTION OF EMBODIMENTS

First Embodiment

An ultrasonic transducer device according to a first embodiment is described.

Figure 1A:
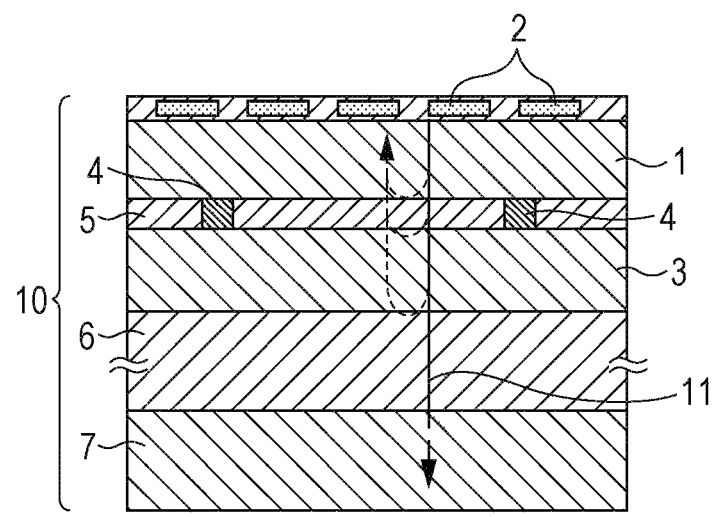
FIG. 1A is a configuration diagram of an ultrasonic transducer device according to any of first to third embodiments of the present invention.

FIG. 1A shows an ultrasonic transducer device 10 according to this embodiment. An electromechanical transducer element 2 is formed on a substrate 1 (first substrate). The electromechanical transducer element 2 provides conversion between an ultrasonic wave (acoustic wave) and an electric signal. An electric wiring substrate 3 (second substrate) is electrically connected with a back surface of the substrate 1. The electric wiring substrate 3 is typically formed by arranging metal wiring lines on resin. A plurality of the electromechanical transducer elements 2 are two-dimensionally arrayed on a front surface of the substrate 1. The electromechanical transducer element 2 may be a piezoelectric element, or a capacitive electromechanical transducer element in which a membrane, a cavity, and first and second electrodes form a counter electrode like PTL 2.

A material of the substrate 1 may be desirably silicon (Si) in view of a mechanical property, an electrical property, formability, cost efficiency, etc. However, the material does not have to be silicon, and may be, for example, glass, quartz, GaAs, or sapphire. The electromechanical transducer element 2 has at least two electric terminals. At least one of the terminals is electrically separated from the plurality of residual electromechanical transducer elements 2. The substrate 1 electrically connects the terminal, which is electrically separated from the electromechanical transducer elements 2 and a terminal on the back surface of the substrate 1. The substrate 1 has, for example, a plurality of electrically connecting portions like through wiring lines. The substrate itself may be electrically separated by an insulator or a trench and the substrate may allow electrical conduction only in a substrate thickness direction.

A conductor 4 that electrically connects the electric wiring substrate 3 and the substrate 1 may be a resistor with a low resistance of, for example, metal such as solder or gold.

In this embodiment, a first acoustic matching layer 5 is arranged between the substrate 1 (first substrate) and the electric wiring substrate 3 (second substrate) and also an acoustic attenuating member 7 is arranged on a backside of the electric wiring substrate 3. The first acoustic matching layer 5 has a function of allowing the electric wiring substrate 3 to transmit an ultrasonic wave 11 that enters from the substrate 1 and restricting reflection of the ultrasonic wave 11. The acoustic attenuating member 7 has a function of absorbing and attenuating the transmitted ultrasonic wave 11. A second acoustic matching layer 6 is provided as a structure that restricts reflection of the ultrasonic wave 11 between the acoustic attenuating member 7 and the electric wiring substrate 3.

With the configuration of the embodiment, noise applied to the electromechanical transducer elements 2 can be reduced in a wider frequency band by reducing the reflection at the interface and by the effect of the acoustic attenuating member.

The first acoustic matching layer 5, the second acoustic matching layer 6, and the acoustic attenuating member 7 are described below in detail.

The first acoustic matching layer 5 fills a space surrounding the conductor 4. In general, an acoustic impedance of the conductor 4 does not correspond to an acoustic impedance of the first acoustic matching layer 5. Hence, an acoustic characteristic varies depending on whether provided directly below the electromechanical transducer element 2 is the first acoustic matching layer 5 or the conductor 4. The area occupied by the conductor 4 is desirably decreased to equalize acoustic characteristics of the electromechanical transducer elements 2.

However, if the acoustic impedance of the conductor 4 is larger than an acoustic impedance of the substrate 1, the ultrasonic wave transmitted to the electric wiring substrate 3 is reduced, and also transmission of the ultrasonic wave reflected by the electric wiring substrate 3 to the substrate 1 is reduced. If the substrate 1 is made of silicon and the conductor 4 is made of typical lead-free solder, the above relationship is applied. The influence of the reflection wave to the electromechanical transducer element 2 on the conductor 4 is small.

A plurality of the conductors 4 is provided on the back surface of the substrate 1 by at least a number corresponding to the number of electromechanical transducer elements 2 to electrically separate the two-dimensionally arrayed electromechanical transducer elements 2. Hence, part of a space between the substrate 1 and the electric wiring substrate 3 not occupied by the conductors 4 is filled with the first acoustic matching layer 5.

The acoustic impedance of the first acoustic matching layer 5 is designed to be a value between the acoustic impedance of the substrate 1 and an acoustic impedance of the electric wiring substrate 3.

A material of the first acoustic matching layer 5 is desirably epoxy resin, which is used as an underfill (sealant). However, when the acoustic impedance is adjusted, a material with high-density fine particles mixed may be used. The fine particles may be a metal or a compound. For example, tungsten, alumina, copper, or a compound of any of these metals; or platinum, iron, or a compound of any of these metals may be used.

The second acoustic matching layer 6 is provided on a back side of the electric wiring substrate 3, and the acoustic attenuating member 7 is provided below the second acoustic matching layer 6. The second acoustic matching layer 6 has a role of reducing acoustic reflection at the back surface of the electric wiring substrate 3, and allowing the acoustic attenuating member 7 to transmit the ultrasonic wave.

A material of the second acoustic matching layer 6 may be epoxy resin or the like, which is the material of the electric wiring substrate 3. However, it is to be noted that, since the acoustic impedance of the electric wiring substrate 3 varies depending on density of the metal wiring lines, adjustment for an acoustic impedance of the second acoustic matching layer 6 is occasionally required. If required, high-density fine particles are mixed to adjust the acoustic impedance. The fine particles may be a metal or a compound. For example, tungsten, alumina, copper, or a compound of any of these metals; or platinum, iron, or a compound of any of these metals may be used.

The acoustic attenuating member 7 has an effect of absorbing and attenuating an ultrasonic wave. Hence, the acoustic attenuating member 7 is a viscoelastic body, and a material of the acoustic attenuating member 7 may be, for example, epoxy resin or urethane resin.

To increase the degree of freedom for design on a back side of the acoustic attenuating member 7, almost all acoustic waves should be attenuated by the acoustic attenuating member 7. To attain this, the acoustic attenuating member 7 has to have a thickness of about several millimeters or larger, and a larger thickness is more desirable. Also, a material having a higher viscosity is more desirable.

Figure 1B:
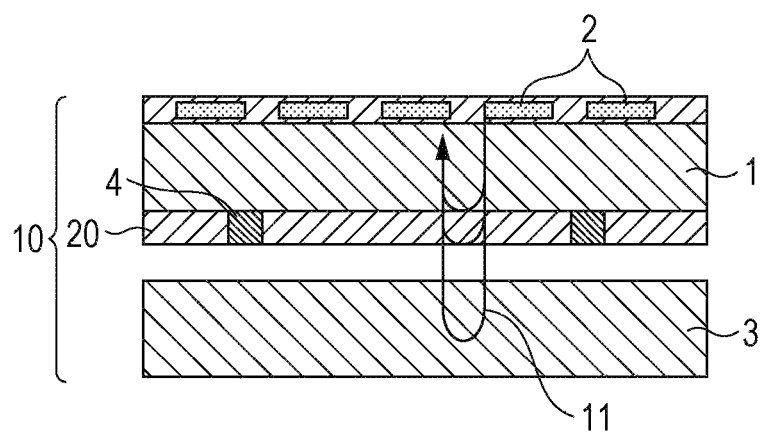
FIG. 1B is a comparison diagram with the first embodiment of the present invention.
Figure 2:
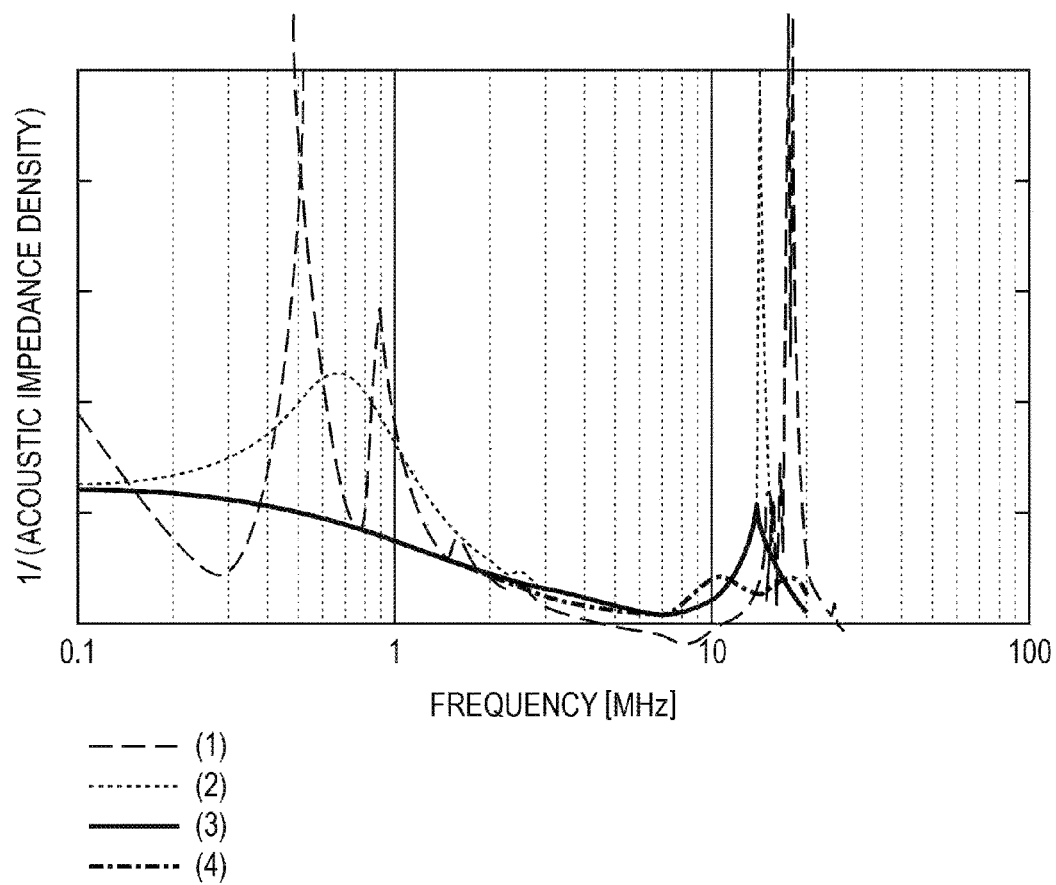
FIG. 2 is a graph showing frequency characteristics for reciprocals of acoustic impedance densities on a front surface of a substrate according to the first embodiment of the present invention.

FIG. 2 shows frequency characteristics of reciprocals of acoustic impedance densities in an acoustic-wave incident direction on the front surface of the substrate 1. An acoustic impedance density corresponds to an input impedance when viewed from the front surface of the substrate 1. For example, if the substrate 1 is silicon with a thickness of 300 micrometers and the electric wiring substrate 3 is glass epoxy with a thickness of 1.6 millimeters, the graph shows reciprocals of acoustic impedance densities (1) when liquid with an acoustic impedance of about 1.5 MegaRayls, for example, water is present between the substrate 1 and the electric wiring substrate 3 and on the back side of the electric wiring substrate 3 (FIG. 1B), (2) when a member with the same acoustic impedance as that of the electric wiring substrate 3 is provided by an infinite thickness at the back side of the electric wiring substrate 3, and (3) when a first acoustic matching layer with an acoustic impedance of 5 MegaRayls is provided between the substrate 1 and the electric wiring substrate 3. Part of the electric wiring substrate 3 is connected with the substrate 1 through the conductor 4, and the distance between the substrate 1 and the electric wiring substrate 3 is limited. In the graph in FIG. 2, the distance is 0.2 millimeters.

When the reciprocal of the acoustic impedance is large, it represents that the reflection wave is large. A large peak with a frequency of 10 MHz or higher indicates resonant reflection by the substrate 1. FIG. 1B shows a configuration of (1) in FIG. 2. The ultrasonic wave 11 transmitted through the electromechanical transducer element 2 resonates as the result of reflection at an interface between the back surface of the substrate 1 and liquid 20, an interface between the liquid 20 and the electric wiring substrate 3, and the lower surface of the electric wiring substrate 3, and propagates to the front surface of the substrate 1 on which the electromechanical transducer element 2 is present. Accordingly, the acoustic impedance density of frequencies around 1 MHz is decreased and becomes a factor that causes large reflection noise. It is found from FIG. 2 that a reflection wave around 1 MHz is decreased by matching of acoustic impedances at the back surface of the electric wiring substrate 3. However, a frequency band with large reflection waves is present around 1 MHz ((2) in FIG. 2). Regarding (3) provided with the first acoustic matching layer 5, it is found that the peak around 1 MHz is lowered, and the reflection wave in the low-frequency region is reduced by the first acoustic matching layer 5 and the acoustic attenuating member 7. This represents that the ultrasonic wave 11 transmitted through the respective layers is absorbed and attenuated by the acoustic attenuating member 7 as shown in the propagation state of the ultrasonic wave 11 in FIG. 1A.

Second Embodiment

An ultrasonic transducer device according to a second embodiment is described. A configuration of this embodiment is the same as that shown in FIG. 1A. For a center frequency of an ultrasonic wave emitted from the electromechanical transducer element 2, when the first acoustic matching layer 5 has a thickness that is ¼ of a wavelength of an ultrasonic wave that is transmitted through the inside of the first acoustic matching layer 5 and when the acoustic impedance of the first acoustic matching layer 5 is a geometric average of the acoustic impedance of the first substrate 1 and the acoustic impedance of the electric wiring substrate 3, a transmission factor of the ultrasonic wave becomes maximum.

If there is an ultrasonic wave with a frequency that should not be reflected the most (or that should be attenuated), the thickness of the first acoustic matching layer 5 may be ¼ of a wavelength of that ultrasonic wave. In particular, if a frequency band of ultrasonic waves to be received is a wide band, frequencies that result in large reflection are frequencies subject to resonant reflection by the substrate 1. (4) in the graph in FIG. 2 represents this case. Regarding (4), it is found that a peak with 15 MHz, which is a resonant frequency, is further lowered.

It is assumed that Zs is an acoustic impedance of the substrate 1, Zm is an acoustic impedance of the first acoustic matching layer 5, and Ze is an acoustic impedance of the electric wiring substrate 3. When L is a thickness of the first acoustic matching layer 5, and k is the number of waves of the ultrasonic wave, a reflection factor R of the ultrasonic wave at a three-layer structure including the substrate 1, the first acoustic matching layer 5, and the electric wiring substrate 3 is expressed as follows.

$$R = \frac{Zin - Zs}{Zin + Zs} \quad \text{[Math. 1]}$$

$$Zin = Zm \cdot \frac{Ze + jZm \tan kL}{Zm + jZe \tan kL} \quad \text{[Math. 2]}$$

When kL is p/2, i.e., when L is ¼ of a wavelength, R becomes minimum. Also, in the following situation, R becomes 0 and all waves are transmitted.

$$Zm = \sqrt{Zs \cdot Ze} (=Z0) \quad \text{[Math. 3]}$$

When the reflection factor is 10% or lower, and a tolerance of the acoustic impedance of the first acoustic matching layer is within about 5% of Z0, a tolerance of the thickness L is within about 6% of the thickness that is ¼ of the wavelength. Since the relationship between the reflection factor R and the noise to the electromechanical transducer element 2 affects the structure, the reflection factor R cannot be simply determined. However, in the embodiment, the reflection factor R is within a range of 10% or lower.

Third Embodiment

An ultrasonic transducer device according to a third embodiment is described. A configuration of this embodiment is similar to that shown in FIG. 1A. The acoustic impedance of the first acoustic matching layer 5 has a gradient in the thickness direction. Impedance matching is provided at the interface between the substrate 1 and the electric wiring substrate 3. Accordingly, the reflection wave can be reduced regardless of the thickness of the first acoustic matching layer 5.

In the embodiment, the provision of the acoustic impedance matching represents a situation in which a reflection factor at an interface is 10% or lower. If acoustic impedances of two substances that form an interface are the same, the reflection factor becomes zero. The situation in which the reflection factor is 10% or lower is a situation in which the difference between the acoustic impedances of the two substances at the interface is about 18% or lower.

The material of the first acoustic matching layer 5 according to this embodiment is fabricated by mixing high-density particles into resin.

By changing particle density distribution in the thickness direction, the acoustic impedance has a gradient in a thickness direction.

Fourth Embodiment

Figure 3:
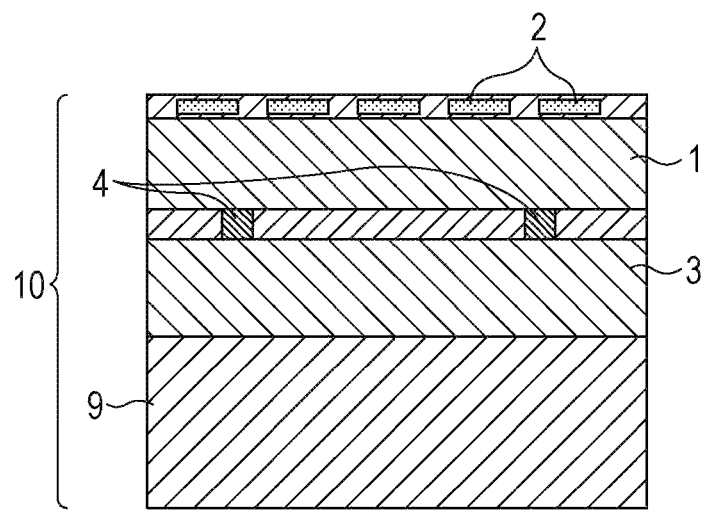
FIG. 3 is a configuration diagram of an ultrasonic transducer device according to a fourth embodiment of the present invention.

An ultrasonic transducer device according to a fourth embodiment is described. FIG. 3 shows a configuration of this embodiment. In this embodiment, the second acoustic matching layer 6 and the acoustic attenuating member 7 in the first or third embodiment are integrated (structure in which the second acoustic matching layer 6 also functions as the acoustic attenuating member 7), and are formed as an acoustic matching and attenuating member 9. At this time, acoustic impedance matching is desirably provided between the acoustic matching and attenuating member 9 and the electric wiring substrate 3.

Here, the provision of the acoustic impedance matching represents a situation in which the reflection factor is 10% or lower. If acoustic impedances of two substances that form an interface are the same, the reflection factor becomes zero. The situation in which the reflection factor is 10% or lower is a situation in which the difference between the acoustic impedances of the two substances at the interface is about 18% or lower.

A material of the acoustic matching and attenuating member 9 may be a viscoelastic body such as urethane resin that contains high-density fine particles for acoustic impedance adjustment. The fine particles may be a metal or a compound. For example, tungsten, alumina, copper, or a compound of any of these metals; or platinum, iron, or a compound of any of these metals may be used.

Fifth Embodiment

An analyte information acquiring apparatus according to a fifth embodiment is described.

Figure 4:
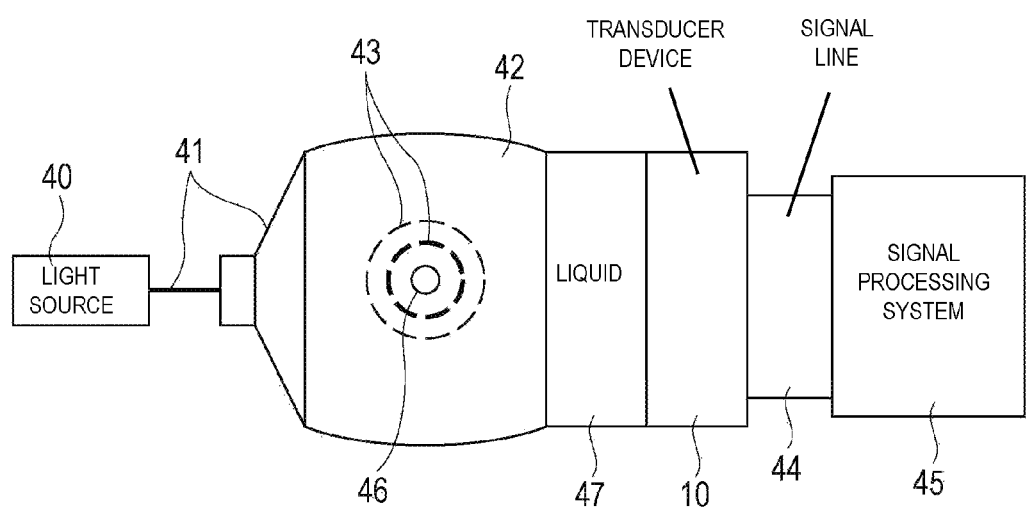
FIG. 4 is a configuration diagram of an ultrasonic diagnostic apparatus according to a fifth embodiment of the present invention.
Figure 5:
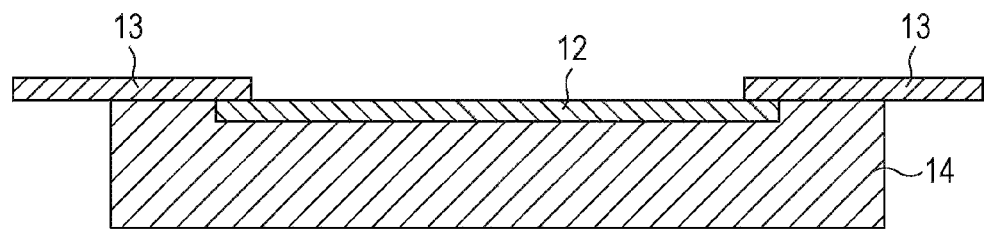
FIG. 5 is a configuration diagram of related art.

FIG. 4 shows a configuration of this embodiment.

When light 41 emitted from a light source 40 is emitted on an optical absorber 46 in an analyte 42, an ultrasonic wave 43 called a photoacoustic wave is generated. Although the frequency of the ultrasonic wave 43 varies depending on a substance of the optical absorber 46 and the size of a solid body, when a certain variation band is assumed, frequencies are within a range from about 300 kHz to 10 MHz. The ultrasonic wave 43 passes through liquid 47 that provides good propagation for the ultrasonic wave 43, and the ultrasonic transducer device 10 detects the ultrasonic wave 43. A signal with amplified current and voltage is transmitted to a signal processing system 45 through a signal line 44. The signal processing system 45 processes the detected signal and extracts analyte information.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST 1 substrate
2 electromechanical transducer element
3 electric wiring substrate
4 conductor
5 first acoustic matching layer
6 second acoustic matching layer
7 acoustic attenuating member
9 acoustic matching and attenuating member
10 ultrasonic transducer device
11 ultrasonic wave

The invention claimed is:

1. An electromechanical transducer device, comprising:
a first substrate having electromechanical transducer elements configured to provide conversion between acoustic waves and electric signals, two-dimensionally arrayed on a first surface side of the first substrate;
an electric wiring substrate that is a second substrate electrically connected with the electromechanical transducer elements, and is located on a second surface side being a back side of the first surface which is opposite the first surface side of the first substrate; and
a first acoustic matching layer provided between the first substrate and the second substrate, containing electrically connecting parts between the first substrate and the second substrate, wherein the first acoustic matching layer having an acoustic impedance larger than that of the second substrate such that a reflection of an acoustic wave entering from the first substrate is restricted.

2. The electromechanical transducer device according to claim 1, wherein the electromechanical transducer elements include capacitive electromechanical transducer elements having a vibrating membrane and a cavity.

3. The electromechanical transducer device according to claim 1, wherein the acoustic impedance of the first acoustic matching layer is smaller than that of the first substrate.

4. The electromechanical transducer device according to claim 1, wherein the first acoustic matching layer contains a resin.

5. The electromechanical transducer device according to claim 4, wherein the first acoustic matching layer contains the resin and fine particles.

6. The electromechanical transducer device according to claim 1, further comprises an acoustic attenuating layer provided on an opposite side of the second substrate to the first substrate side, the acoustic attenuating layer absorbs and attenuates the acoustic wave transmitted through the second substrate.

7. The electromechanical transducer device according to claim 6, wherein the acoustic attenuating layer contains a resin.

8. The electromechanical transducer device according to claim 6, further comprising a second acoustic matching layer provided between the second substrate and the acoustic attenuating layer, wherein the second acoustic matching layer restricts a reflection of the acoustic wave between the second substrate and the acoustic attenuating layer.

9. The electromechanical transducer device according to claim 1, wherein the first substrate has a plurality of through wiring lines.

10. An analyte information acquiring apparatus, comprising:
the electromechanical transducer device according to claim 1;
a light source configured to emit pulsed light; and
a signal processing system configured to process a signal that is detected by the electromechanical transducer device,
wherein the analyte information acquiring apparatus irradiates an analyte with the light emitted from the light source, detects an acoustic wave generated as the result of a photoacoustic effect of the light emitted on the analyte by the electromechanical transducer device, and acquires physical information of inside of the analyte through processing by the signal processing system.

11. The electromechanical transducer device according to claim 1, wherein the acoustic impedance of the first acoustic matching layer has a gradient in the thickness direction.

12. The electromechanical transducer device according to claim 11, wherein the acoustic impedance matching is provided at the interface between the first substrate and the first acoustic matching layer.

* * * * *